United States Patent [19]

Palmenberg et al.

[11] Patent Number: 4,937,190
[45] Date of Patent: Jun. 26, 1990

[54] TRANSLATION ENHANCER

[75] Inventors: Ann C. Palmenberg; Gregory M. Duke; Parks, Griffith D., all of Madison, Wis.

[73] Assignee: Wisconsin Alumni Research Foundation, Madison, Wis.

[21] Appl. No.: 109,132

[22] Filed: Oct. 15, 1987

[51] Int. Cl.$^5$ .................. C12P 21/00; C12P 19/34; C12N 15/00

[52] U.S. Cl. .................. 435/69.1; 435/68.1; 435/70.1; 435/70.3; 435/172.1; 435/172.3; 435/91; 935/4; 935/6; 935/32; 935/33; 935/34

[58] Field of Search .............. 435/68, 172.1, 172.3, 435/235, 91; 536/27; 935/4, 6, 32, 34, 44

[56] References Cited

PUBLICATIONS

Semler et al., (1986), PNAS 83:1777–1781.
G. Parks et al., 60 J. Virol., 376–384, (Oct. 17, 1986) (not prior art).
H. Krausslich et al., 61 J. Virol., 2711–2718, (1987) (not prior art).
G. Parks et al., 61 J. Virol. (in press) (Dec. 1987).
K. Chumakov et al., 246 Dokl. Biochem., 209–212, (1979).
F. Golini et al., 287 Nature, 600–603, (1980).
D. Shih et al., 30 J. Virol., 472–480, (1979).
S. Gupta et al., 144 Virol., 523–528, (1985).
H. Pelham, 85 Eur. J. Biochem., 457–461, (1978).
A. Palmenberg et al., 32 J. Virol., 770–778, (1979).
A. Palmenberg et al., 41 J. Virol., 244–249, (1982).
R. Rueckert et al., 78 Meth. Enzym., 315–325, (1981).
C. Shih et al., 40 J. Virol., 942–945, (1981).
A. Palmenberg, 44 J. Virol., 900–906, (1982).
A. Palmenberg et al., 12 Nucl. Acid. Res., 2969–2985, (1984).
R. Rueckert et al., 50 J. Virol., 957–959, (1984).
Racaniello et al., 214 Science, 916–919, (1981).
G. Parks et al., "In Vitro Proteolytic Processing of EMC Clones", Jun. 22–26, 1986, American Society For Virology Annual Meeting, University of California, Santa Barbara, Calif., (title only).
G. Duke et al., "Transcription and Translation of EMC cDNA Clones In Vitro", Jun. 22–26, 1986, American Society For Virology Annual Meeting, University of California, Santa Barabara, Calif., (title only).

Primary Examiner—Richard A. Schwartz
Assistant Examiner—Anne Brown
Attorney, Agent, or Firm—Quarles & Brady

[57] ABSTRACT

Disclosed in this patent are DNA sequences, RNA sequences, vectors, and hosts that incorporate a translation enhancer region derived from the 5' non-coding region of a cardiovirus. The enhancer acts at the RNA level (as opposed to the DNA level) to enhance production of proteins in cell free media. Proteinaceous material which is produced will not have attached to it any undesired material from the enhancer sequence. The invention is especially useful to enable efficient production of selected viral proteins of picornoviruses.

9 Claims, 1 Drawing Sheet

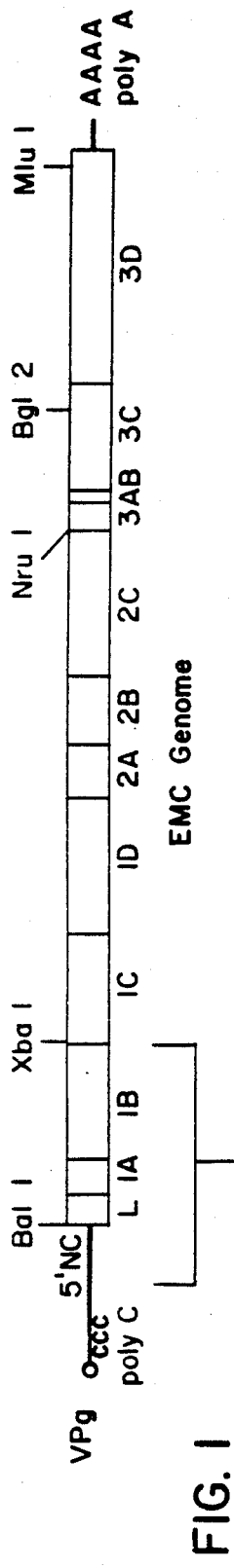

FIG. 1

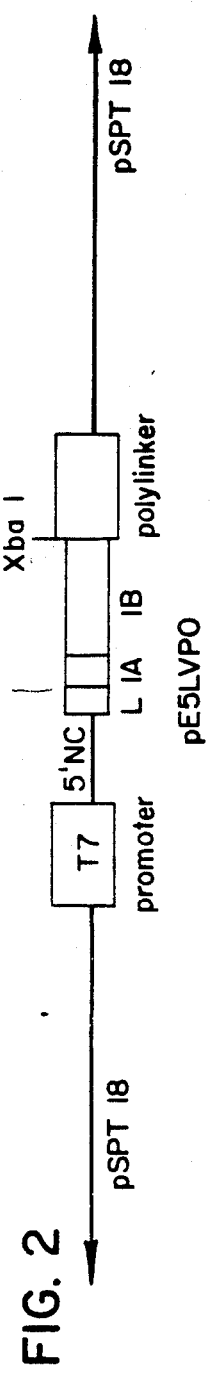

```
  1  UUG....                                                                    ....C
241  GCUUG GAAUA AGGCC GGUGU GCGUU UGUCU AUAUG UUAUU UCCAC CAUAU UGCCG UCUU     300
301  UUGGC AAUGU GAGGG CCCGG AAACC UGGCC CCUGU CCCUG CCCUU CUUGU GAGCA CAUUC CUAGG GGUC  360
361  UUUCC CCUCG CCAAA GGAAU GCAAG GUCUG UUGAA UGUCG UGAAG GAAGC AGUUC CUC      420
421  UGGAA GCUUC UUGAA GACAA ACAAC GUCUG UAGCC GUAUA AGCGA CCCUU GCAGG GAACC CCC  480
481  CACCU GGCGA CAGGU GCCUC UGCGG CCUCG CCCAA AGCCA CGUGU AUAAG AUACA CCUGC AAGG  540
541  CGGCA CAAAC CCCCA GUGCC ACGUU GUGAG UUGGA UAGUU GUGGA AAAGU GGCUC UAUCC CCACC  600
601  CCUCA AGCGU AUUCA ACAAG GGGCU GAAGG AUGCC CAGAA GGUAC CCCAU UGUAU GGGAU  660
661  CUGAU CUGGG GCCUC GGUGC ACAUG CUUUA CAUGU GUUUA GUCGA GGUUA AAAAC GUCU   720
721  AGGCC CCCCG AACCA CGGGA CGUGG UUUUC CUUUG AAAA ACACG AUGAU AAUAU GGCCA    780
                                                                 MetAlaT        840
```

TRANSLATION ENHANCER

The present invention relates to a picornaviral genetic sequence that is capable of improving the efficiency of translation of RNA into proteinaceous material. More particularly, it relates to a 5' non-coding cardiovirus nucleotide sequence capable of enhancing such translation in cell free media.

BACKGROUND OF THE INVENTION

With the increasing use of genetic engineering techniques, commercial scale production of many proteinaceous materials has become possible. Once a protein becomes available in large quantity, researchers can then more easily study it and its function, and they can use it for other purposes that require relatively large quantities of the protein. Of course, even where commercial scale production techniques are available, there is always a desire to lower the cost and time involved in the production of such proteins.

One technique that the art has tried to make production more efficient is to locate efficient DNA promoter sequences that occur in nature, and then use them in order to improve the efficiency of "transcription" of DNA to RNA. Another approach has been to develop means to culture eukaryotic host cells, so as to provide suitable hosts to permit "translation" (RNA to protein) of certain proteins that need host proteins to be expressed. This approach is costly, involves separation problems, and is not universally applicable.

Yet another approach is to create "cell free" extracts (e.g. derived from rabbit reticulocytes) so as to provide an in vitro media for translation of RNA to proteinaceous material. See e.g. D. Shih et al., 30 J. Virol. 472-480 (1979); S. Gupta et al., 144 Virol. 523-528 (1985). The disclosure of these articles (and all of the other articles recited herein) are incorporated by reference as if fully set forth below. Unfortunately, in vitro translation of certain RNA (e.g. polio virus and rhinovirus) has been inefficient in such media.

In the past, researchers have conducted general research into various viruses known as cardioviruses. These picornavirus RNA viruses do not go through a DNA stage in their life cycle. Encephalomyocarditis virus ("EMC"), Mengovirus, Mous-Elberfeld virus, MM virus, and Columbia SK virus are examples of cardioviruses. It has been learned that these viruses have relatively efficient translation of their coding RNA in cell free systems. It has also been learned that there are various techniques for culturing and producing the natural cardioviruses. Some work has also been done on sequencing these viruses. See generally H. Pelham, 85 Eur. J. Biochem. 457-463 (1978); A. Palmenberg et al., 32 J. Virol. 770-778 (1979); A. Palmenberg, 41 J. Virol. 244-249 (1982); R. Rueckert et al., 78 Meth. Enzym. 315-325 (1981); C. Shih et al., 40 J. Virol. 942-945 (1981); A. Palmenberg, 44 J. Virol. 900-906 (1982); A. Palmenberg et al., 12 Nucl. Acid. Res. 2969-2985 (1984); R. Rueckert et al., 50 J. Virol. 957-959 (1984); K. Chumakov et al., 246 Dokl Biochem 209-212 (1979).

SUMMARY OF THE INVENTION

In one aspect of the invention there is provided a DNA sequence coding for an RNA translational enhancer. The enhancer has the characteristics of a cardiovirus RNA translational enhancer sequence that is located 5' of a cardiovirus AUG sequence. Preferably, the RNA translational enhancer is of the non-coding type, the cardiovirus is encephalomyocarditis, and the DNA sequence has the characteristics of an encephalomyocarditis translational enhancer coding region in ATCC 67525. A host, e.g. E. coli, can contain the DNA sequence.

In another aspect of the invention, there is provided a recombinant DNA vector. The vector has a DNA transcriptional promoter and a DNA enhancer coding sequence capable of coding for an RNA translational enhancer. The enhancer has the characteristics of a cardiovirus RNA enhancer sequence that is located 5' of a cardiovirus AUG sequence. The DNA enhancer coding sequence is positioned on the vector so as to be subject to the transcriptional promoter. There is also a foreign DNA gene (e.g. one capable of producing a foreign proteinaceous material of interest) which is positioned on the vector so as to be subject to the transcriptional promoter and so that after transcription of the foreign DNA gene and the DNA enhancer coding sequence to their RNA variants, translation of the RNA variant of the foreign DNA gene will be subject to the control of the RNA variant of the enhancer coding sequence.

In a preferred form, the RNA translational enhancer is of the non-coding type, the cardiovirus is encephalomyocarditis, the foreign DNA gene does not code for a cardiocvirus protein, and the enhancer coding sequence has the characteristics of an encephalomyocarditis translational enhancer coding region in ATCC 67525.

In yet another aspect of the invention, a recombinant RNA sequence is provided. It has an RNA translational enhancer of the noncoding type which in turn has the characteristics of a cardiovirus RNA translational enhancer sequence that is located 5' of a cardiovirus AUG sequence (and preferably 3' of a poly C tract). There is also provided a foreign RNA sequence linked to the enhancer so as to be subject to the control of the enhancer.

In another embodiment of the invention, there is provided a method of producing a desired proteinaceous material. According to the method, one expresses, in vitro, in a cell free media, the above foreign RNA sequence using the recombinant RNA sequence.

An object of the invention therefore is to provide DNA and RNA sequences, vectors, and hosts of the above kind which can be used to improve RNA translation efficiency.

Another object of the invention is to provide DNA and RNA sequences, vectors, and hosts of the above kind, together with methods for their use, to enable a desired proteinaceous material to be produced in vitro, in a cell free media, without extraneous enhancer coding sequences being attached to the proteinaceous material which is produced.

Another object of the invention is to provide an improved means of expressing virion proteins of picornaviruses.

Still other objects and advantages of the present invention will be apparent from the description which follows.

DESCRIPTION OF THE FIGURES

FIG. 1 shows a schematic depiction of the encephalomyocarditis RNA genome;

FIG. 2 shows a schematic depiction of a DNA plasmid incorporating the DNA variant of an enhancer of the present invention; and FIG. 3 shows the RNA nucleotide sequence of nucleotides 1-3 and 260-840 of the EMC genome.

DESCRIPTION OF THE PREFERRED EMBODIMENTS

It should be understood that the descriptions of the preferred embodiments below are merely examples of the invention. They are not intended to represent the full scope of the invention. Rather, the claims should be looked to in order to determine the full scope of the invention.

The RNA genome of EMC is shown in FIG. 1. The first 834 nucleotides of the almost 8000 EMC RNA nucleotides are noncoding nucleotides located 5' of the AUG coding initiation site. Over 200 of these 834 nucleotides are repetitive C's (the poly C tract). The open box portions of FIG. 1 represent the coding portions of the genome. Also shown are the positions of some restriction sites of interest.

CONSTRUCTION OF A RECOMBINANT DNA VECTOR

The research which led to the present invention is described in somewhat greater detail than below in G. Parks et al., 60 J. Virol. 376-384 (Oct. 17, 1986) (not prior art). Restriction enzymes were purchased from New England Biolabs. DNA manipulations were done using standard methods. See e.g. T. Maniatis et al., Molecular Cloning: A Laboratory Manual, Cold Spring Harbor, Laboratory (1982). All transformations to ampicillin resistance were performed with E. Coli HB101 obtained from Promega Biotec, Madison, Wis.

Culturing and purification of EMC viral RNA was as described in R. Rueckert et al., 78 Meth. Enzym. 315-325 (1981). Random length RNA segments were created with various restriction enzymes. To change viral RNA segments to double stranded DNA, reverse transcription procedures analogous to those reported in A. Palmenberg et al., 12 Nuc. Acid Res. 2969 (1984) were followed. EcoRI DNA linkers (New England Biolabs) were then ligated to the ends of the double-stranded DNA, and the resulting material was inserted into the EcoRI site of the transcription vector pSPT18 (Pharmacia Fine Chemicals). Plasmid pSPT18 is a derivative of plasmid pUC18 containing a T7 transcriptional promoter sequence and a polylinker cloning site. (See FIG. 2)

One of the resulting plasmids, plasmid pE3Tll contained EMC sequences originating from within the poly(C) tract and extending 3' about 2,300 bases past the AUG into the coregion encoding viral peptide VP3. To construct plasmid pE5LVP0, DNA from plasmid pE3Tll (1 µg) was digested with XbaI to completion. After extraction with phenol-chloroform and precipitation with ethanol, the DNA was reacted with T4 DNA ligase to reform the plasmid, and a portion of the mixture was used to transform E. coli HB101. The resulting colonies were screened for the size of the EMC segment. One plasmid was chosen and designated pE5LVP0. It contains DNA corresponding to nucleotides 260 through 2004 of EMC RNA. pE5LVP0 in E. coli C600 Amp[R] has been deposited with the American Type Culture Collection, Rockville, Md., with ATCC #67525. It will be made available as required under applicable patent law. Such availability is not intended as a license to practice the invention.

As shown in FIG. 3, nucleotides 834-36 are the AUG coding initiation sequence. AUG in RNA corresponds to ATG in DNA and ATGGCCA on the DNA includes the BalI site TGGCCA. Thus, after digestion of the plasmid with XbaI and BalI, a plasmid is derived with no EMC coding regions, and a foreign gene can be inserted at the cut point, followed by ligation to recircularize.

An easier alternative is to provide a desired DNA foreign gene with a terminator sequence, and then insert it at the BalI site of pE5LVP0. For example, DNA (4 µg) from a full-length clone of polio type I Mahoney virus (Racaniello, et al., 214 Science 916-919 (1981)) can be digested with NruI (2 units) for 15 hours at 37° C, followed by digestion with SmaI (5 units) at 30° C for 12 hours. The resulting fragment is ligated for 12 hours at 12° C with 10 units of T4 DNA ligase and 0.5 µg of plasmid pE5LVP0, which has previously been digested with 2 units of BalI for 12 hours at 37° C. What is formed by this latter technique is a recombinant plasmid vector with a transcriptional promoter T7, followed by a DNA translational enhancer non-coding region, a foreign DNA gene (in this case the 3' half of the polio type I Mahoney coding region), a terminator, and then the rest of the plasmid.

To transcribe the DNA to RNA, purified plasmid DNA is linearized by digestion with XbaI restriction enzyme. After extraction with phenol-chloroform and precipitation with ethanol, the samples were suspended in water. Typically, about 1 µg of linear plasmid DNA was transcribed in reactions (25 µl) with T7 RNA polymerase as specified by the enzyme manufacturer (Bethesda Research Laboratories), except that the ribonucleotides and dithiothreitol were increased to 1mM and 25 mM, respectively. RNase inhibitor (RNasin; Promega Biotec) was also included (1.5 U/ µl). After incubation at 37° C for 1 h, the samples were extracted with phenolchloroform, precipitated with ethanol, dried under 7 vacuum, and suspended in water (10 µl; estimated concentration, 1 µg/µl).

In vitro translation reactions in reticulocyte extracts were carried out in a manner analogous to the procedures of D. Shih et al., 30 J. Virol. 472-480 (1979). Typically, 3 to 5 µl of plasmid transcription product (see above) was used to direct cell-free protein synthesis reactions (30 µl) radiolabeled with [35S]methionine (specific activity, 1,100 Ci/mmol; final concentration, 1 Ci/µl). After 40 min. at 30° C, reactions were stopped by addition of pancreatic RNase and cycloheximide (to 0.3 mg/ml each).

This technique can be used to produce a single EMC virion protein (as opposed to the naturally occurring string of EMC proteins). See G. Parks et al., 60 J. Virol. 376-387 (1986) (not prior art). This opens up the possibility of research directed to particular EMC proteins. For example, the availability of large quantities of EMC proteins such as the protease 3C will permit such proteins to be used in assays to screen for drugs that block the activity of the proteins (and thus block the activity of the virus). In this regard, a protease splits other compounds. By exposing a given quantity of such a protein to a possible drug in the presence of a substance that it usually effects (e.g. cleaves), chromatographic and/or other techniques can determine which if any compounds inhibit protein activity. Because many viruses have protease sequences, and because all picornaviruses appear to have similar protease sequences, the EMC protease assay may act as a screen for drugs for other viral proteases as well. This is important because some viruses are very dangerous to work with in laboratories.

As an alternative, a foreign DNA from poliovirus or another virus, or another non viral source can be inserted. See e.g. H. Krausslich et al., 61 J. Virol. 2711–2718 (1987) (not prior art).

It will also be appreciated that while one particular EMC derived enhancer is shown in the drawings, enhancers can be produced synthetically using the coding between nucleotides 488 and 834, or using slight variants of the natural sequence, or using other cardioviruses with similar 5' non-coding regions. Thus, sequences substantially having the characteristics of the EMC sequence are intended to be included in the language "having the characteristics." Further, while polio and EMC viruses have been referred to as the expressed genes, eukaryotic and viral translation may be broadly enhanced by this region.

We claim:

1. A recombinant DNA vector comprising:

a DNA transcriptional promoter;

a DNA enhancer sequence that can be transcribed to a non-coding RNA segment, said RNA segment having an RNA base sequence that also appears in a cardiovirus RNA enhancer base sequence located 3' of a cardiovirus polyC sequence of over 50 base pairs and 5' of a cardiovirus AUG initiation sequence;

said DNA enhancer sequence being positioned on the vector so as to be operatively linked to and promotable by said DNA transcriptional promoter; and a foreign DNA gene coding for a desired proteinaceous material, said gene being positioned on the vector so as to be operatively linked to and promotable by a transcriptional promoter and being positioned so that after transcription of the foreign DNA gene and the DNA enhancer sequence, translation of a RNA transcription resultant of the foreign DNA gene can occur.

2. The vector of claim 1, wherein the cardiovirus is encephalomyocarditis.

3. The vector of claim 2, wherein the foreign DNA gene codes for other than cardiovirus protein.

4. A recombinant RNA sequence, comprising:

an RNA translational enhancer which is non-coding and has a RNA base sequence that also appears in a cardiovirus RNA translational enhancer base sequence located 3' of a cardiovirus polyC sequence of over 50 base pairs and 5' of a cardiovirus AUG initiation sequence; and a foreign RNA sequence linked to the enhancer so translation of the foreign RNA can occur.

5. The recombinant RNA sequence of claim 4, wherein the cardiovirus is encephalomyocarditis.

6. The recombinant RNA sequence of claim 5, wherein the enhancer has a sequence which is identical to an RNA sequence that can be created by transcription of an xba I fragment of encephalomyocarditis DNA sequence contained in the material deposited as ATCC 67525.

7. A method for producing a desired proteinaceous material comprising the step of expressing in vitro, in a cell free media, the foreign RNA sequence of the recombinant RNA sequence of claim 5.

8. A host containing the DNA vector of claim 1.

9. A recombinant vector comprising:

a DNA vector sequence from other than cardiovirus linked to a DNA sequence that can be transcribed to a non-coding RNA translational enhancer, said RNA translational enhancer having an RNA base sequence that also appears in a cardiovirus RNA base translational enhancer sequence located 3' of a cardiovirus polyC sequence of over 50 base pairs and 5' of a cardiovirus AUG initiation sequence.

* * * * *